United States Patent [19]

Tohyama

[11] Patent Number: 4,566,793
[45] Date of Patent: Jan. 28, 1986

[54] RECORDING APPARATUS FOR A SPECTROPHOTOMETER

[75] Inventor: Shigeo Tohyama, Katsuta, Japan
[73] Assignee: Hitachi, Ltd., Tokyo, Japan
[21] Appl. No.: 552,762
[22] Filed: Nov. 17, 1983

[30] Foreign Application Priority Data

Nov. 17, 1982 [JP] Japan ................................ 57-201752

[51] Int. Cl.⁴ .............................................. G01J 3/42
[52] U.S. Cl. .................. 356/319; 346/33 A; 346/34; 346/62
[58] Field of Search ............... 356/319, 320, 323, 325; 346/33 A, 34, 62

[56] References Cited

U.S. PATENT DOCUMENTS

| | | | |
|---|---|---|---|
| 3,344,702 | 10/1967 | Wood et al. | 346/62 X |
| 3,840,878 | 10/1974 | Houston et al. | 346/62 |
| 3,949,408 | 4/1976 | Mason et al. | 346/62 |
| 4,074,273 | 2/1978 | Dupree et al. | 346/34 |

OTHER PUBLICATIONS

Bulletin 7255–"Beckman ACTA M UV/VIS–NIR Spectrophotometers", 1974.

Primary Examiner—F. L. Evans
Attorney, Agent, or Firm—Antonelli, Terry & Wands

[57] ABSTRACT

A spectrophotometer to draw time changes of a plurality of spectrophotometric data by one recording pen. The spectrophotometer has a plurality of sample cells for accommodating samples to be optically measured and for enabling repeated optical measurement of each sample in a certain time interval, a timer for providing a time when the sample is measured, a first memory section for respectively memorizing each pair of the repetitive measured data and time, a second memory section for memorizing the data indicative of the source point of the movement of the pen and the data representative of the destination point among each of the pairs memorized in the first memory section, an arithmetic logical unit to calculate the difference between the destination point data and source point data and to provide an output of the calculation, a pen-controller for moving the pen in response to the output of the arithmetic logical unit, and a sheet-controller for receiving the output of the arithmetic logical unit and for moving a recording sheet synchronously with the movement of the pen by the pen-controller.

7 Claims, 10 Drawing Figures

DATA

| 1 | 2 | 3 |
|---|---|---|
| 0.9873 Abs | 0.3456 Abs | 0.2234 Abs |
| 0.8880 Abs | 0.3658 Abs | 0.3356 Abs |
| 0.7654 Abs | 0.3860 Abs | 0.4424 Abs |
| 0.6543 Abs | 0.4070 Abs | 0.5683 Abs |
| 0.5432 Abs | 0.4290 Abs | 0.6821 Abs |
| 0.4321 Abs | 0.4320 Abs | 0.7964 Abs |
| 0.3220 Abs | 0.4350 Abs | 0.9133 Abs |

DELTA

| | | |
|---|---|---|
| 0.0993 | −0.0202 | −0.1122 |
| 0.1226 | −0.0202 | −0.1068 |
| 0.1111 | −0.0210 | −0.1259 |
| 0.1111 | −0.0220 | −0.1138 |
| 0.1111 | −0.0030 | −0.1143 |
| 0.1111 | −0.0030 | −0.1169 |

FIG. 10

RECORDING APPARATUS FOR A SPECTROPHOTOMETER

BACKGROUND OF THE INVENTION

1. Field of the Invention

The present invention relates to a recorder to record the states in that a plurality of measured values change as the time elapses and, more particularly, to a recording apparatus to indicate a plurality of measured values by lines.

2. Description of the Prior Art

In many fields of analyzing equipment and measuring apparatuses, a plurality of kinds of measured values are indicated on the same recording sheet or same screen. For example, an example whereby four kinds of measured values are drawn on one sheet of recording paper by the same pen is disclosed in "Beckman ACTA M UV/Vis-NIR Spectrophotometers" issued in 1974 Bulletin 7255, pp. 13. In this way, a method is known whereby the spectroscopic characteristics of a plurality of samples are measured by the photometer and the states in that the measured values of the respective samples change with the time are indicated on the same recording sheet or same screen.

Figure 1:
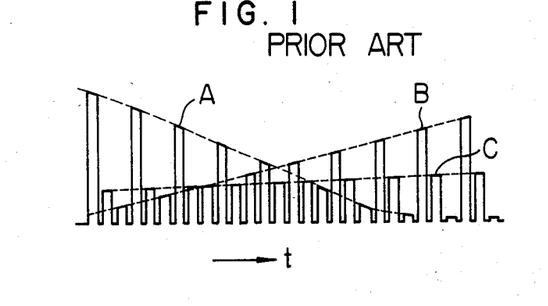
FIG. 1 is a diagram showing a recording example by a conventional recorder.

A display example by a conventional display apparatus is shown in FIG. 1. The states in that the measured values of samples A, B and C change as the time elapses are indicated by the bar graphs as shown by the solid lines. Since these bar graphs are difficult to see the change states of the respective samples, the change amounts of the respective samples are read out manually after indication and each measured value of each sample is connected by the line as shown by the broken lines.

As described above, in a conventional recording apparatus, it is difficult to see the indication using bar graphs and this has to be processed manually.

Since these measurements necessitate several hours, it is preferable to automatically measure and record the spectrophotometric data.

SUMMARY OF THE INVENTION

It is an object of the present invention to solve such drawbacks in a conventional recording apparatus and to provide a recording apparatus which is suitable to indicate the states of time changes of the measured values of a plurality of samples by the lines, respectively.

Another object of the present invention is to provide an apparatus which can automatically print the measured values and measuring axes all together.

According to the present invention, the above object is accomplished by a spectrophotometer comprising: a data memory section to memorize time change data of a plurality of spectrophotometerically measured values; a data storage section to preserve the data at two time points of certain measured values among the above-mentioned plurality of data; a display section to indicate by coupling the above-mentioned data at the two time points by a line; and a timing control section to control these memory, storage and display sections with predetermined timings.

This spectrophotometer is constituted as described above and reads out the measured values from the memory section in which the measured values which change with the time of two or more samples were memorized or from the memory which reads such values with the time and memorizes them, thereafter it overlappingly indicates the measured values on the same recording sheet or screen. In the case where the measured values are on-line displayed in association with the measuring operation, they are coupled by the lines when no measurement is performed.

By controlling the display section with a predetermined timing by the timing central section, it is possible to change the form of the display line for every measuring sample, such as, for example, solid line, broken line, or alternate long and short dash line. Furthermore, when the time changes of the measured values of a plurality of samples are coupled by the lines, if it is difficult to see them since they are overlapped, the display section is controlled by the timing control section so that they can be easily seen by changing over the scale of the measuring axis in dependence upon the samples. The timing control section can also print the measured values.

DESCRIPTION OF THE PREFERRED EMBODIMENTS

Figure 2:
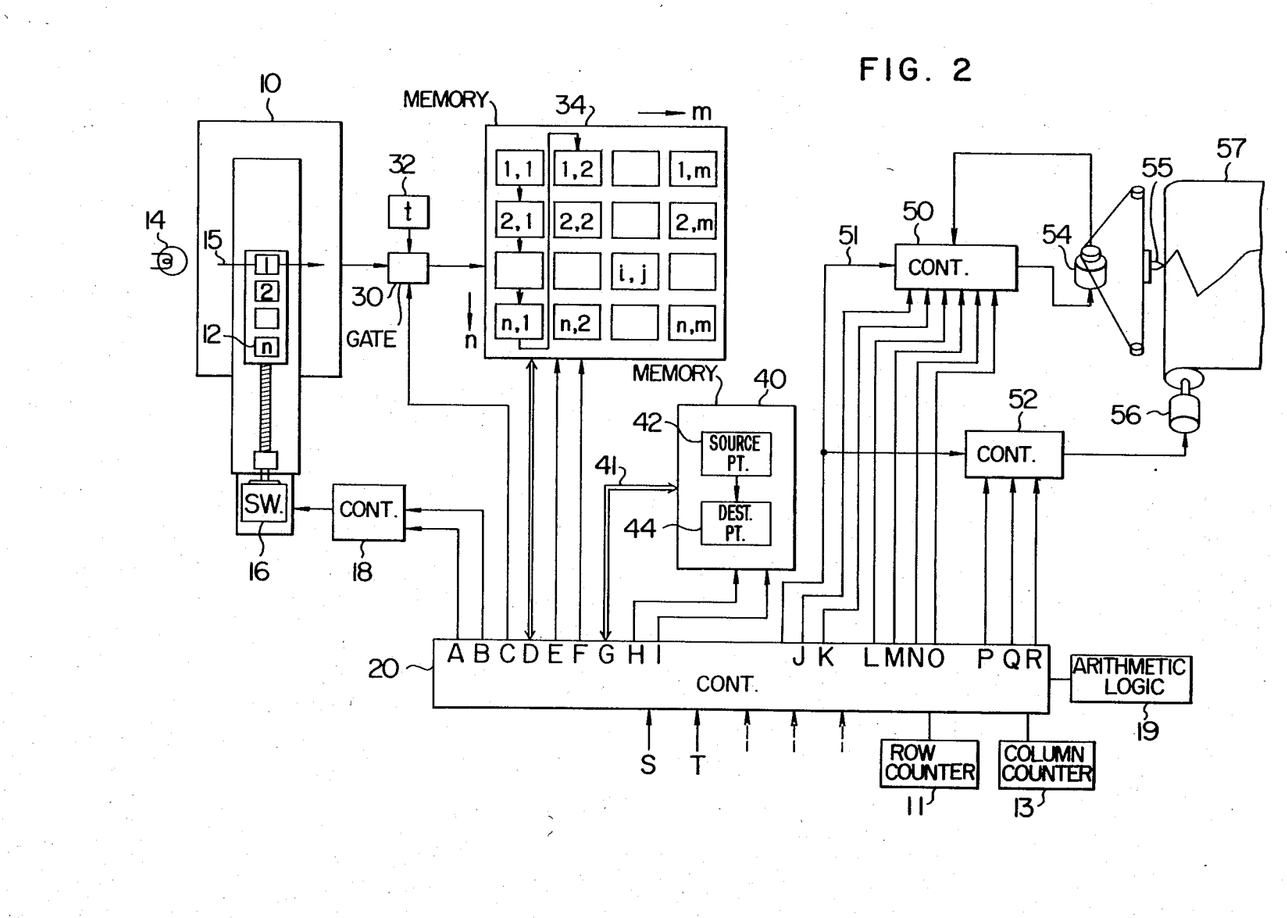
FIG. 2 is a block diagram of a display apparatus as one embodiment according to the present invention.

Referring now to FIG. 2, there is shown an example in which the present invention was exemplified as a recorder for a photometer.

A plurality of sample cells 12 (e.g. n cells) are provided in a spectrophotometer 10 so that they are sequentially set into an optical path 15 to be formed by an optical source 14 by a motor 16 for switching sample cells. The sample cell switching motor 16 is controlled by a switching control section 18. A data memory section 34 has a memory capacity of m rows and n columns and memorizes measured values. A data storage section 40 has at least two memories 42 and 44 and temporarily preserves the measured values at different time points of a certain sample. A motor 54 for driving a recording pen 55 is controlled by a recording pen control section 50. A motor 56 for driving a recording sheet 57 is controlled by a recording sheet control section 52. A timing control section 20 has various kinds of control terminals A to R and external input terminals S and T, thereby controlling the operation timings of the above-mentioned means 12, 34, 40, 54, and 56 in accordance with such a flowchart as shown in FIG. 3.

The operation of the present embodiment will now be described with reference to FIGS. 2 and 3. The memory section 34 has a memory capacity in which the matrix arangement of m rows and n columns is possible, and it is possible to store each pair of times and measured values of m times, which indicate the number of measurement repetition times, for each of n samples.

Figure 3:
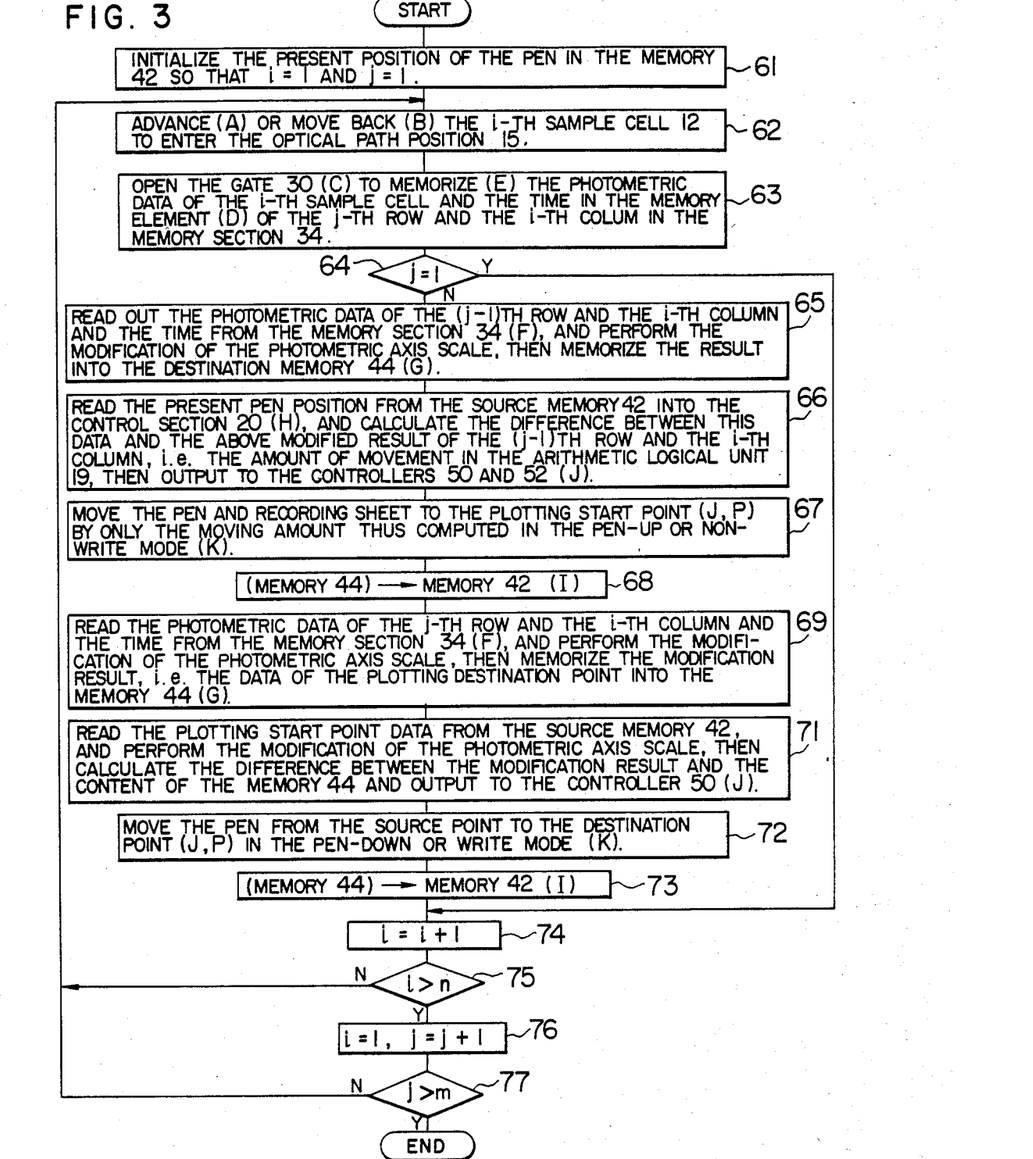
FIG. 3 is a flowchart showing the operations of the present invention.

Prior to the measurement, in block 61 of FIG. 3, variables j and i in a row counter 11 and a column counter 13 in the control section 20 are set to 1, respectively. It is now assumed that the pen 55 moves from a certain source point to a certain destination point on the recording sheet 57. The source memory 42 memorizes the source point and the destination memory 44 memorizes the destination point.

Pressing a measurement start button (not shown) by an operator allows the i-th sample cell 12, i.e. if i=1, the first sample cell to be advanced (A) or moved back (B) to enter the position of the optical path 15 in block 62. At this time, the present position of the pen 55 and the starting time are also memorized in the memory 42. Now, alphabets A, B, etc. correspond to the input/output terminals A, B, etc. of the control section 20 of FIG. 2 and to A, B, etc. in each block of the flowchart of FIG. 3, respectively. In block 63, the timing control section 20 resets the timer 32 and generates a command to open a gate 30 from the control terminal C. The photometric data of the i-th sample cell together with the time from a timer 32 is memorized (E) from the terminal D through the address and data buses to the memory element of the j-th row and the i-th column, i.e. if i=j=1, the (1,1)th memory element in the memory section 34. In block 64, the measurement is discriminated whether it is the first time or two or more times. In other words, the measuring and recording operations of the loop of blocks 62, 63, 64, 74, and 75 are carried out one time by one with respect to n samples while advancing (A) the sample cells 12.

Thereafter, the variable i in the counter 13 becomes larger than n and as the result of discrimination in block 75, the resetting operation of the counter is executed in block 76, and then the operation advances to the second-time optical measuring operation of each sample. In block 62, the control section 20 generates a command to cause the motor 16 for switching the sample cells to reversely rotate to the switching control section 18, thereby allowing the cell to be moved back (B). Thus, the first sample 12 is again set into the position on the optical path of the light source 14.

After discrimination block 64, in block 65, the control section 20 sends a readout command from the terminal F to read out (D, F) a pair of measured data of the (j−1)th row and the i-th column and the time, namely if j=2, and i=1, a pair in the first row and the first column from the memory section 34 through the address and data buses D. Then, they are memorized in the destination memory 44 (G) in response to a memory command from the terminal H. This measured data may be memorized after performing the calculation of addition, subtraction, multiplication, and division in accordance with the display scale selected in response to a range of data variation. In block 66, the control section 20 serves to read out the data indicative of the present position of the pen which has been prepared in block 61 from the source memory 42 through the address and data buses 41 (G, H). An arithmetic logical unit 19 computes the difference between this position data and the former data in the memory 44 and at the same time it computes the difference between the times. The control section outputs these calculation results to the controllers 50 and 52 through a line 51 (J, K, P, Q). Reference characters J and K represent the terminals to command the forward and reverse rotations of the motor 54, respectively. P and Q denote the terminals to command the forward and reverse rotations of the recording sheet driving motor 56. In block 67, the controllers 50 and 52 output the pulses of the number corresponding to the position difference and time difference which were thus computed as described above in a known manner to the pulse motors 54 and 56, respectively, thereby moving the pen and recording sheet to the plotting start point (J, P) in the pen-up state or non-write mode (K).

Thereafter, the content of the memory 44 is transferred to the memory 42 in block 68 (I). This means that the former destination now becomes the start point for movement.

In block 69, the control section 20 reads out the photometric data and time from the memory section 34 (F) and performs the modification of the photometric axis scale if it is required, thereby creating the plotting destination point data and memorizes in the memory 44 (G).

In block 71, the control section 20 reads out the plotting start point data from the source memory 42, and performs the modification of the photometric axis scale if it is necessary, then it calculates the difference between this data read out and the content of the memory 44 and outputs the result to the controller 50 (J). If the difference between the measurement times is constant throughout a series of measurements, it may be possible to omit the calculation of time difference among the computations performed in block 66.

In block 72, the pen moves from the start point to the destination point simultaneously together with the recording sheet in the pen-down state or write mode. The content of the memory 44 is transferred to the memory 42 in block 73.

After the recording between two points of the first sample has been finished, the addition of i=i+1 is performed in block 74, this means that the operation of the apparatus is moved to the next sample cell. In the same manner as described above, this adding operation of one is continued until the recordings of the n samples are finished.

Generally, the j-time measured value of the i-th sample together with the measurement time is memorized in the address of the j-th row and the i-th column.

Figure 6:
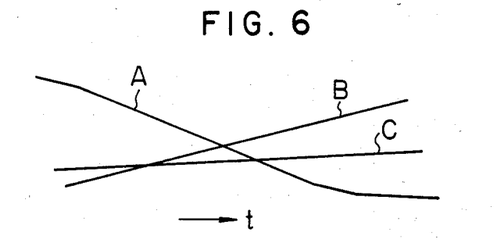
FIG. 6–9 are diagrams showing recording examples which were recorded by the display apparatus as the embodiment according to the present invention.

FIG. 6 shows recording examples with respect to samples A, B and C on the basis of the above-described operations. It will be appreciated that the time changes of the respective samples can be more easily read from this drawing as compared with the recording charts of FIG. 1.

Figure 7:
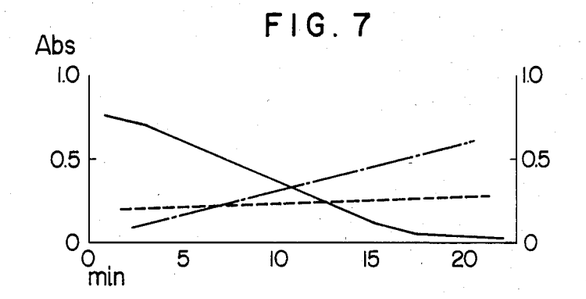

Although all of the recording lines were shown by the solid lines in the recording examples shown in FIG. 6, if one desires to change the kinds of recording lines in dependence upon the samples in order to further easily observe these diagrams, it is possible to specify the mode of the recording line, such as the broken line, alternate long and short dash line, etc. from, e.g. the control terminals M and N by instructing from the external input terminal S. FIG. 7 shows recording examples whereby the kinds of recording lines are changed in dependence upon the samples. The felt pen is used as the recording pen. This recording pen may be a thermal pen. The term "pen-down" means the energization and the term "pen-up" denotes the non-energization.

Figure 8:
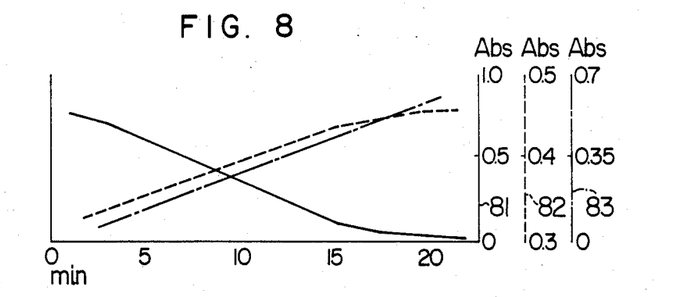
Figure 9:
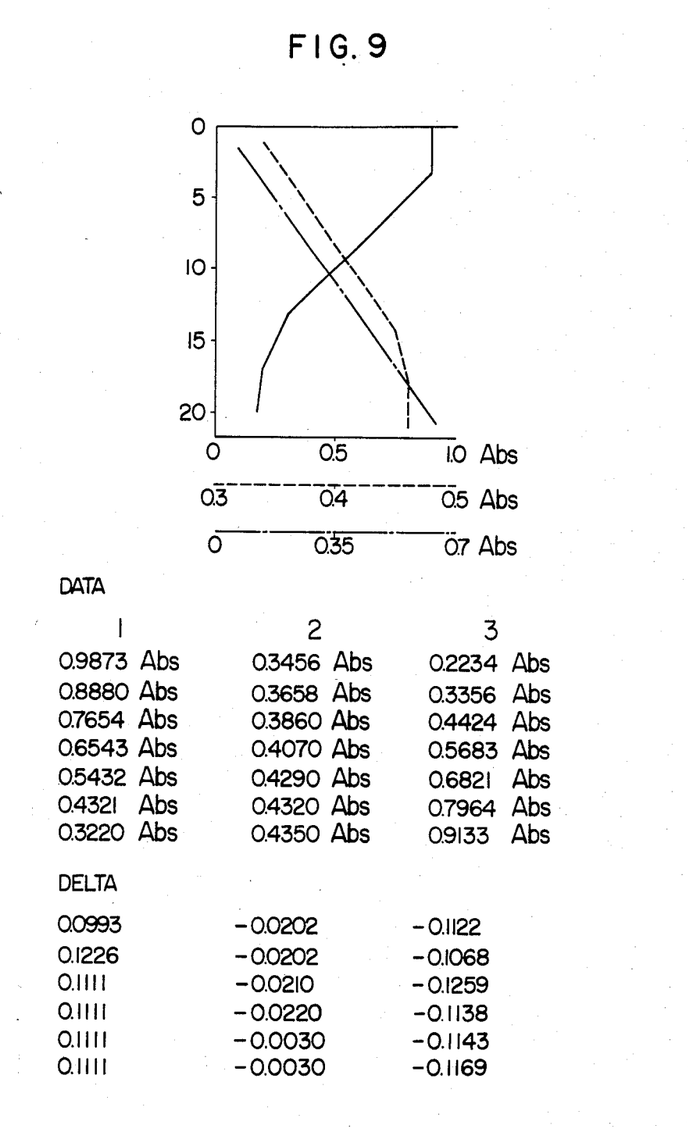

Next, if one desires to change the scales of the respective recording lines in dependence upon the samples, the instruction is sent from the external input terminal T and the changes of magnifications of the movements are instructed from the control terminals O and R to the respective controllers 50 and 52, thereby enabling the scales of measuring axes to be changed. FIG. 8 shows examples recorded by this operation. Three photometeric axes 81–83 of FIG. 8 shows the ranges of the scales which were specified by the operator before starting the measurements, respectively. Furthermore, if the recording pen can print, after measurements, it is also possible to directly read the measured values from the memory section 34 to the recording pen control section and to print the numerals of the measured values and measuring axes. Such examples thus printed are shown in FIG. 9.

Although the examples to record using the recording pen have been described in the above embodiment, the display by a CRT is also possible. Furthermore, in the present embodiment, the embodiment in that the apparatu is interconnected to the outputs of the spectrophotometer has been described; however, the memory section 34 is not limited to that in this embodiment, but an off-line type in which the measured values have been preliminarily memorized may be used.

Figures 4, 5:
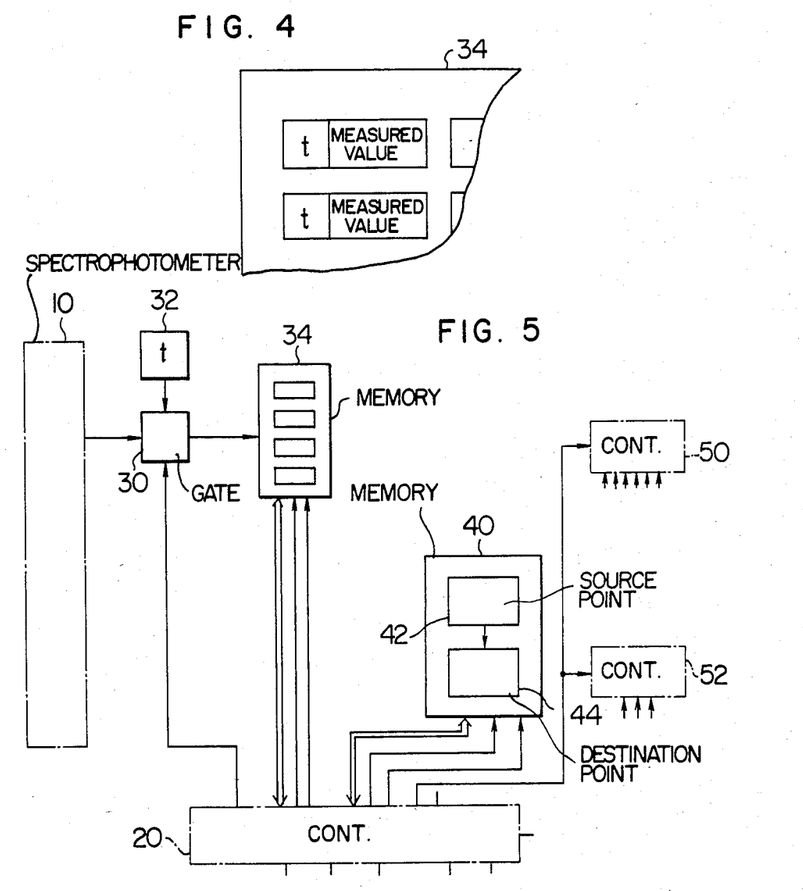
FIG. 4 is a diagram showing the memory format of a memory section in the embodiment shown in FIG. 1.
FIG. 5 is a partial block diagram to describe another embodiment according to the present invention.

In addition, the memory section 34 does not necessarily memorize all of the measured values (measured values of m times with respect to n samples), for example as shown in FIG. 4, such a constitution that n memories corresponding to the number of samples are used may be adopted. In such a case, the content of the memory section 34 is erased every time when the data is transferred from the memory section 34 to the storage section 40, thereafter new data is sequentially taken. It may be possible to adopt such a constitution that the measured values at the second and subsequent times with respect to each sample from the photometer are taken in the memory section 34 and at the same time they are taken in the memory section 44 on the destination side.

Although the sample cells 12 shown in FIG. 2 are the linearly reciprocating type, it may be possible to use such a type that a circular sample cells are rotated.

Although the recorder of the flowchart type has been described in the present embodiment, it can be easily analogized that the present invention can be accomplished even in the X-Y plotting recorder in which the recording pen moves in the X and Y directions.

The recording of the change amount of one cycle is started simultaneously when the input of the (n+1)th photometric value is started according to the present invention; however, even in this embodiment, it is also possible to accomplish the means for recording the data after all of the measurements were finished without recording during measurement since the data is memorized even after the measurements have been finished. Moreover, the change amount can be also recorded after printing.

Although the example in which the change amount of each sample in each cycle is recorded has been mentioned in the present invention, it can be easily analogized from the constitution of the present invention that the change amount from a particular eigenvalue (e.g., change amount from the photometeric values of each sample at the first time or from the eigenvalue which has been preset) is recorded.

Figure 10:
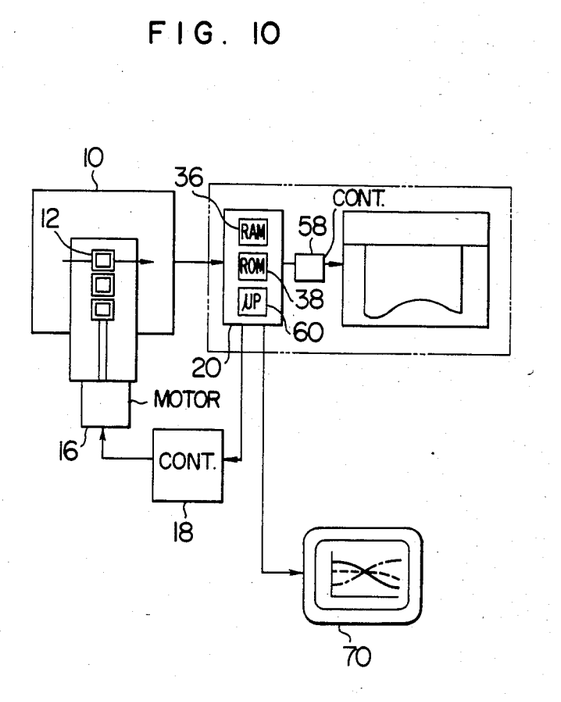
FIG. 10 is a block diagram of a display apparatus as another embodiment according to the present invention.

FIG. 10 shows another embodiment of the present invention, in which the memory devices such as the start position memory device 42, memory section 34, etc. in FIG. 2 are equipped in an RAM 36, and the timing control and other logical processings are programmed and memorized in an ROM 38, thereby carrying out the processing by a microprocessor 60 and controlling a pen via controller 58. Furthermore, it can be easily analogized that graphs and photometeric values can be displayed by equipping a CRT 70.

1. A spectrophotometer to draw time changes of a plurality of spectrophotometric data by one recording pen, comprising:
   a plurality of sample cells for accommodating samples to be optically measured, each of said samples being repeatedly optically measured in a certain time interval;
   a timer for providing a time when said sample is measured;
   a first memory section for respectively memorizing each pair of said repetitive measured data and time;
   a second memory section for memorizing data indicative of a source point of the movement of said pen and data representative of a destination point among each of said pairs memorized in said first memory section;
   an arithmetic unit to calculate a difference between both measurement data for said destination point and source point and a time difference between said both measurement data and to provide an output of the calculation;
   a controller for moving the pen in response to the output of said arithmetic unit; and
   a controller for receiving the time difference from said arithmetic unit and for moving a recording sheet by an amount corresponding to the time difference synchronously with the movement of the pen by said controller after moving the recording sheet to a position corresponding to the previous measurement time for a currently measured sample with the pen in an up-state.

2. A spectrophotometer according to claim 1, further comprising:
   a counter for counting said plurality of samples; and
   means connected to said counter for changing the form of the recording line to be drawn by said pen for said sample.

3. A spectrophotometer according to claim 1, further comprising:
   means for drawing a plurality of photometric axes to the photometric data of said plurality of samples.

4. A spectrophotometer according to claim 1, wherein
   said arithmetic unit and said controllers cause the measurement recording to on-line operate immediately in response to the memorizing of each of said pairs in said first memory section.

5. A spectrophotometer according to claim 1, wherein
   said pen is a thermal pen.

6. A spectrophotometer according to claim 1, wherein
   said pen is a felt pen.

7. A spectrophotometer to draw time changes of a plurality of spectrophotometric data by one recording pen, comprising:
   a plurality of sample cells for accommodating samples to be optically measured, each of said samples being repeatedly optically measured in a certain time interval;
   a timer for providing a time when said sample is measured;
   a first memory section for respectively memorizing each pair of said repetitive measured data and time;
   a second memory section for memorizing data indicative of a source point of the movement of said pen and data representative of a destination point among each of said pairs memorized in said first memory section;

an arithmetic unit to calculate the difference between both measurement data for said destination point and source point and the time difference between said both measurement data and to provide an output of the calculation;

a controller for moving the pen in response to the output of said arithmetic unit after moving the pen to the source point with the pen in an up-state;

a controller for receiving the time difference from said arithmetic unit and for moving a recording sheet by an amount corresponding to the time difference synchronously with the movement of the pen by said controller after moving the recording sheet to a position corresponding to a previous measurement time for a predetermined one of said samples with the pen in an up-state; and a controller for transferring within said second memory section said data indicative of the destination point to the position for memorizing said data indicative of the source point and for incorporating subsequent data from said first memory section to the position for memorizing said data of the destination point within said second memory section after the movements of the pen and the recording sheet.

* * * * *